United States Patent [19]

Heckele

[11] Patent Number: 4,593,682
[45] Date of Patent: Jun. 10, 1986

[54] ENDOSCOPE

[75] Inventor: Helmut Heckele, Knittlingen, Fed. Rep. of Germany

[73] Assignee: Richard Wolf GmbH, Fed. Rep. of Germany

[21] Appl. No.: 653,705

[22] Filed: Sep. 24, 1984

[30] Foreign Application Priority Data

Sep. 28, 1983 [DE] Fed. Rep. of Germany ... 8327753[U]

[51] Int. Cl.$^4$ ............................................... A61B 1/06
[52] U.S. Cl. ..................................................... 128/6
[58] Field of Search ....................................... 128/4, 6

[56] References Cited

U.S. PATENT DOCUMENTS 3,677,262  7/1972  Zukowski ............................... 128/6
3,776,222  12/1973  Smiddy .................................. 128/6
3,889,662  6/1975  Mitsui ................................... 128/6
4,430,996  2/1984  Bonnet ................................ 128/4 X Primary Examiner—William H. Grieb
Attorney, Agent, or Firm—Hill, Van Santen, Steadman & Simpson

[57] ABSTRACT

The endoscope for the observation and examination of bodily cavities is equipped with uninterrupted image and light ducts and divided into a rigid distal longitudinal member equipped with a handle, and a flexible longitudinal member joined thereto and comprising an eyepiece and a light duct connector. A pair of closely spaced image ducts may be provided connected to respective objectives and eyepieces to allow for stereoscopic observation.

9 Claims, 4 Drawing Figures

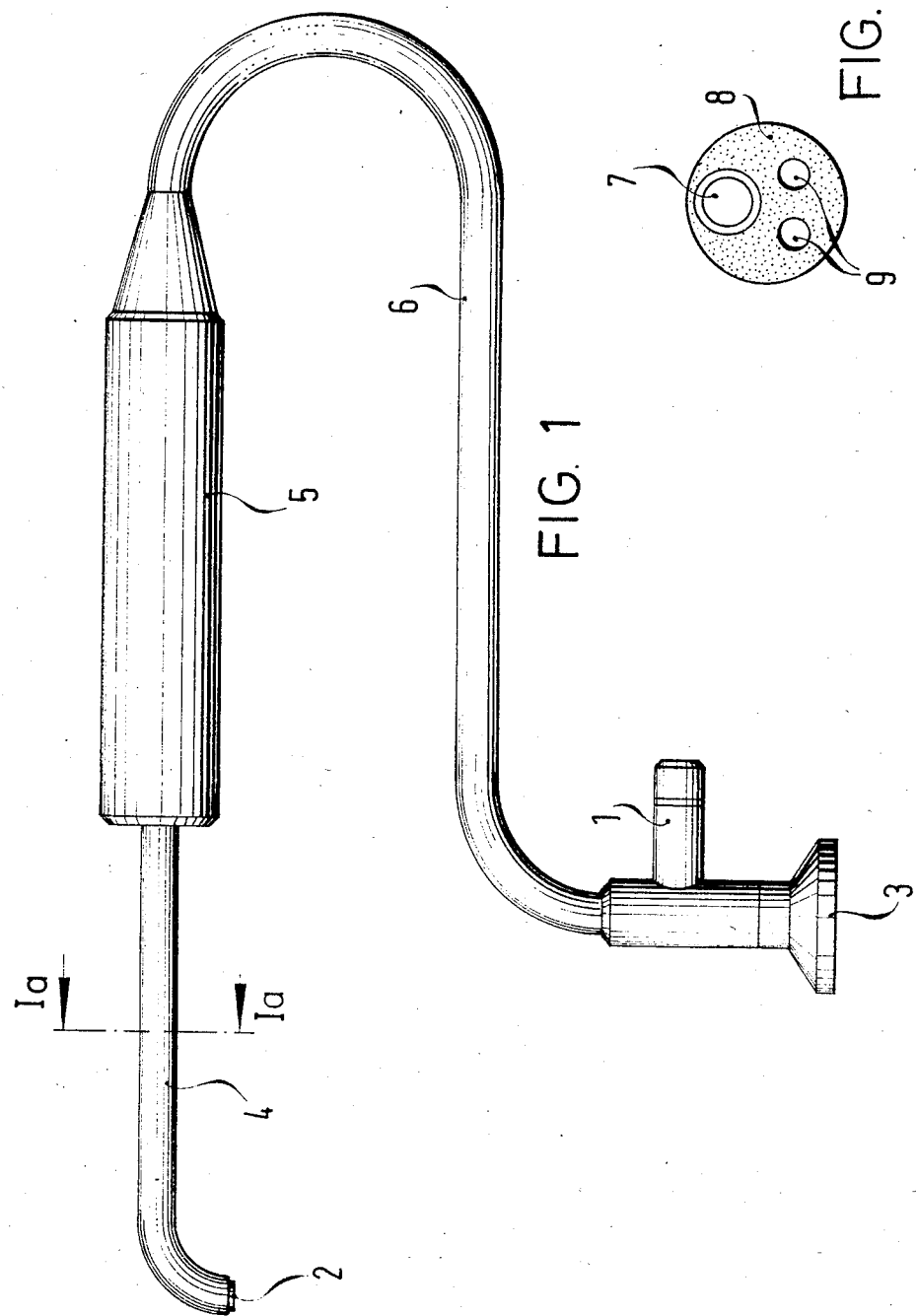

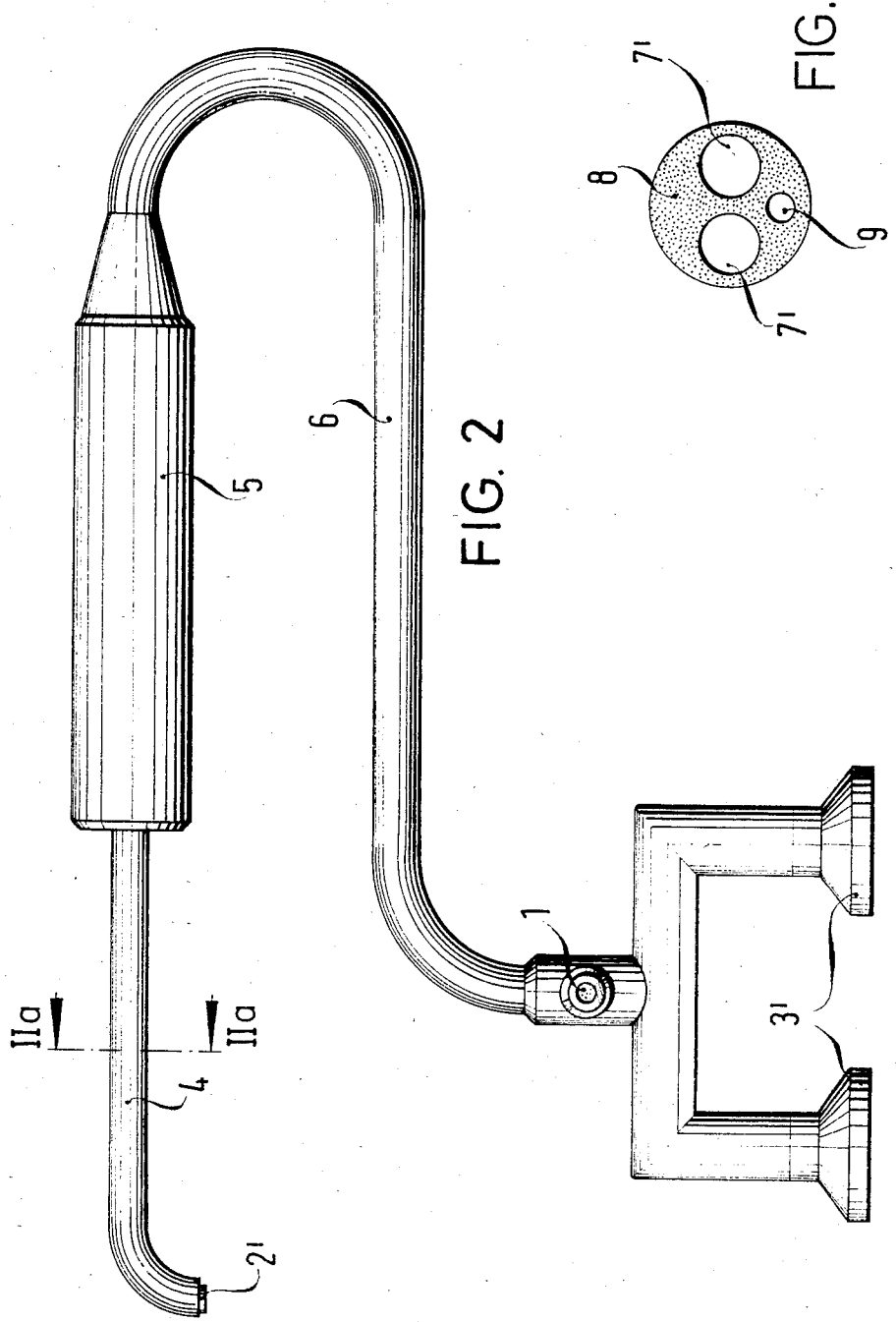

ENDOSCOPE

BACKGROUND OF THE INVENTION

1. Field of the Invention

The invention relates to an endoscope comprising continuous image and light ducts for the observation and examination of bodily cavities, in particular of the prefrontal sinuses.

2. Description of the Prior Art

Endoscopes rigid throughout their length were generally utilised until now for examination of the prefrontal sinuses. For this reason, the examining physician had to assume a very uncomfortable head position under particular circumstances, despite which it was difficult to gain a complete view in areas particularly difficult to reach, so that a limited examination only, was possible. By contrast, completely flexible endoscopes allowed of a complete examination of the prefrontal sinuses, but required onerous handling because of the distal angling over of the endoscope which had to be performed by operation of a handwheel, the flexible endoscope also having to be supported and guided in the area of the prefrontal sinuses.

OBJECTS AND SUMMARY OF INVENTION

The object of the invention consists in constructing an endoscope in a manner such that the physician may maintain a normal head position and that an unimpeded examination of the prefrontal sinuses becomes possible despite this.

A further object is to provide for stereoscopic examination.

A yet further object is to provide access through the endoscope for access of additional instrumentation.

In the case of an endoscope of the kind referred to in the foregoing, this problem is resolved in that the endoscope is divided into a rigid or semi-rigid distal longitudinal member forming a unit with a handle and having a distal extremity and a flexible longitudinal member joined proximally to the handle and having an eyepiece joined to an image duct and a light duct connector.

The distal extremity of the rigid member is suitably angled over or curried to facilitate access into the bodily cavity.

Thanks to this solution, a physician is now able to reach all parts of the prefrontal sinuses with the rigid or semi-rigid distal longitudinal member whilst grasping the handle, which is connected to the flexible proximal longitudinal member to enable him to maintain normal head positions during the examination.

BRIED DESCRIPTION OF THE DRAWINGS

The invention will now be described by way of example with reference to the following diagrammatic drawings:

FIG. 1 is a side view of an endoscope according to the present invention;

FIG. 1a is a cross-sectional view taken on line Ia—Ia of FIG. 1;

FIG. 2 is a side view of an embodiment of the present invention; and

FIG. 2a is a cross-sectional view taken on line IIa—IIa of FIG. 2.

DESCRIPTION OF THE PREFERRED EMBODIMENTS

The endoscope which is traversed in a known manner by a light duct 8 (FIG. 1a) connectible to a light source via a connector 1, and by an image duct 7 (FIG. 1a) having a distal objective lens 2 and a proximal eyepiece 3, is divided into a rigid or semi-rigid distal longitudinal member 4 having a distal extremity which is or may be angled, a handle 5 and a wholly flexible proximal longitudinal member 6 with the eyepiece 3 and and the light connector 1. In this connection, the handle 5 may be rigidly connected to the longitudinal member 6 or coupled releasably to the same. As seen in cross-sectional view of FIG. 1a, a pair of additional open ended passages 9 extend parallel to the image duct 7 through the endoscope and have distal openings in the region of the objective lens 2.

Thanks to the additional possibility of making the distal extremity steerable, and to the utilisation of at least one passage 9 extending parallel to the image duct 7 and to the light duct 8 and having an outlet opening distally in the area of the objective lens 2, it is possible to introduce substances or an auxiliary instrument in a directional manner into the bodily cavity. The proximal light junction connector 1 may be situated either in the handle grip 5 or in the area of the eyepiece 3. Proximal openings of the passages 9, not shown, are arranged for convenient access of an auxiliary instrument into the passageway, for example, at the handle or at a section of the eyepiece, and are suitably provided with connectors.

So as to assure the requirements regarding adequate sterility of the instrument portion 4 to be inserted into the bodily cavity, the rigid member 4,5 and the flexible member 6, are suitably releasably coupled to each other at the proximal extremity of the handle so that the instrument portion 4 may be removed for sterilization.

In a further development of the endoscope, and according to FIGS. 2 and 2a, two image ducts 7' with small mutual spacings are provided in the endoscope, so that it becomes possible to undertake a stereoscopic examination within the abdominal cavity via two eyepieces 3' coupled to respective ducts 7'. It is also possible to exchange the standard objective lens for a wide-angle objective lens, so that a maximum area may be observed.

Whilst the invention and many of its attendant advantages will be understood from the foregoing description, it will be apparent that changes may be made in the form, construction and arrangement of parts without departing from the spirit and scope of the invention.

What is claimed is:

1. In an endoscope having continuous image and light ducts for the observation and examination of body cavities, in particular prefrontal sinuses, the improvements comprising said endoscope being divided into a first relatively rigid distal longitudinal member forming a unit with a handle and having a distal end and a second relatively flexible longitudinal member proximally joined to the handle of the unit and comprising an eyepiece joined to the image duct and a connector for the light duct so that as said handle controls movement of the distal end of the unit into a body cavity, the second flexible member allows relative movement between the handle and eyepiece.

2. In an endoscope according to claim 1, in which the distal end of the first longitudinal member is angled over.

3. In an endoscope according to claim 1, in which the first and second longitudinal members of the endoscope form an indivisible unit.

4. In an endoscope according to claim 1, in which the first and second longitudinal members of the endoscope are releasably coupled to each other in the area of the handle.

5. In an endoscope according to claim 1, wherein said image duct has a distal objective lens and in which at least one open ended passage having an outlet opening situated in the area of the objective lens extends parallel to the image and light ducts traversing the endoscope.

6. In an endoscope according to claim 5, in which the coupling connectors of the light duct and for at least one passage are secured on the handle.

7. In an endoscope according to claim 5, in which coupling connectors for the light duct and at least one passage are secured to a section of the eyepiece.

8. In an endoscope according to claim 1, in which for the purpose of steroscopic observation, the endoscope has two image ducts extending with small spacings from each other, each of the two image ducts having a respective objective lens at the distal side and a respective eyepiece at the proximal side.

9. In an endoscope having continuous image and light ducts for observation and examination of body cavities, in particular prefrontal sinuses, the improvements comprising said endoscope being divided into first and second units, said first unit having a handle with a first relatively rigid longitudinal member extending therefrom and terminating in a distal end of the endoscope, and said second unit comprising a second relatively flexible longitudinal member connected to the handle and extending to a connector for the light duct and to an eyepiece optical joined to the image duct so that both the eyepiece and connector can be moved relative to the handle without disturbing the distal end in a body cavity.

* * * * *